US007532938B2

(12) United States Patent
Machado et al.

(10) Patent No.: US 7,532,938 B2
(45) Date of Patent: May 12, 2009

(54) INTRALUMINAL ELECTRODE ASSEMBLY

(75) Inventors: Sandra Machado, Beachwood, OH (US); Andre Machado, Beachwood, OH (US); Ali Rezai, Shaker Heights, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 538 days.

(21) Appl. No.: 11/222,774

(22) Filed: Sep. 12, 2005

(65) Prior Publication Data

US 2006/0058597 A1 Mar. 16, 2006

Related U.S. Application Data

(60) Provisional application No. 60/608,513, filed on Sep. 10, 2004.

(51) Int. Cl.
*A61N 1/05* (2006.01)

(52) U.S. Cl. ....................................... 607/116; 607/148

(58) Field of Classification Search ................. 607/116, 607/148

See application file for complete search history.

(56) References Cited

U.S. PATENT DOCUMENTS

| | | | |
|---|---|---|---|
| 4,718,423 | A | 1/1988 | Willis et al. |
| 4,776,349 | A | 10/1988 | Nashef et al. |
| 4,976,711 | A | 12/1990 | Parins et al. |
| 5,318,592 | A | 6/1994 | Schaldach |
| 5,411,546 | A | 5/1995 | Bowald et al. |
| 5,653,734 | A | 8/1997 | Alt |
| 5,707,400 | A | 1/1998 | Terry, Jr. et al. |
| 6,058,331 | A | 5/2000 | King |
| 6,266,564 | B1 | 7/2001 | Hill et al. |
| 6,292,695 | B1 | 9/2001 | Webster, Jr. et al. |
| 6,564,096 | B2 | 5/2003 | Mest |
| 2002/0107553 | A1 | 8/2002 | Hill et al. |
| 2003/0004549 | A1 | 1/2003 | Hill et al. |
| 2003/0181951 | A1 | 9/2003 | Cates |
| 2003/0181958 | A1 | 9/2003 | Dobak, III |
| 2003/0216792 | A1 | 11/2003 | Levin et al. |
| 2004/0019364 | A1 | 1/2004 | Kieval et al. |
| 2004/0030362 | A1 | 2/2004 | Hill et al. |
| 2004/0210295 | A1 | 10/2004 | Brushey |
| 2004/0230255 | A1 | 11/2004 | Dobak, III |
| 2005/0149156 | A1 | 7/2005 | Libbus et al. |

(Continued)

OTHER PUBLICATIONS

Janes, RD, et al., "Anatomy of Human Extrinsic Cardiac Nerves and Ganglia", American Journal of Cardiology, 1986; vol. 57; pp. 299-309.

(Continued)

*Primary Examiner*—Carl H Layno
*Assistant Examiner*—Yun Haeng Lee
(74) *Attorney, Agent, or Firm*—Kenyon & Kenyon LLP

(57) ABSTRACT

A minimally invasive intraluminal electrode assembly that includes a cannulated tube and a plurality of wires disposed within the cannulated tube. Each of the plurality of wires has one of a plurality of electrical contacts on a distal end thereof. The distal portion of the plurality of wires assumes a radially constrained configuration within the cannulated tube in a retracted position and a radially extended position outward of the cannulated tube in a deployed position. The electrode assembly further comprises a spring electrode connecting the plurality of electrical contacts to collectively form a substantially circular configuration in a deployed position.

7 Claims, 5 Drawing Sheets

10 30 40a 60 70 20 40e

U.S. PATENT DOCUMENTS

2006/0079945 A1 4/2006 Libbus et al.

OTHER PUBLICATIONS

Murphy DA, et al., "Human Cardiac Nerve Stimulation", The Annals of Thoracic Surgery, vol. 54, 1992, pp. 502.

Heusch G., et al., "Adrenergic Mechanisms in Myocardial Ischemia", Supp. To Basic Research in Cardiology, vol. 85, 1990, Germany.

Vitek, Md, JL., "Mechanisms of Deep Brain Stimulation: Excitation or Inhibition", Movement Disorders, vol. 17, Supp. 3, 2002, pp. S69-S72, Atlanta, GA.

Cooper, TB, et al., "Neural Effects on Sinus Rate and Atrioventricular Conduction Produced by Electrical Stimulation from a Transvenous Electrode Catheter in the Canine Right Pulmonary Artery", circres.ahajournals.org, 2007, vol. 46, 1980, pp. 48-57, Birmingham, Alabama.

Scherlag BJ, et al., "Endovascular Stimulation within the left pulmonary artery to induce slowing of hear rate and paroxysmal atrial fibrillation", Cardiovascular Research, vol. 54, 2002, pp. 470-475.

Levine, RL, Md. et al., "Central Venous and Pulmonary Artery Catheter Monitoring", Critical Care Monitoring from Pre-Hospital to the ICU, pp. 145-158.

Benumof, Md. JL, et al., "Pulmonary Artery Catheterization", in Clinical Procedures in Anesthesia and Intensive Care, JB Lippincott Company, PA, 1992, pp. 405-441.

Matthay, Md., MA, et al., "Bedside Catheterization of the Pulmonary Artery: Risks Compared with Benefits", in Clinical Procedures in Anesthesia and Intensive Care, JB Lippincott Company, vol. 109, 1988; pp. 826-834.

Hillier, SC., "Monitored Anesthesia Care", Clinical Anesthesia, Chapter 47, 2001, pp. 1239-1254.

Hudson, RJ., "Basic Principles of Clinical Pharmacology", Clinical Anesthesia, Chapter 11, 2001, pp. 239-260.

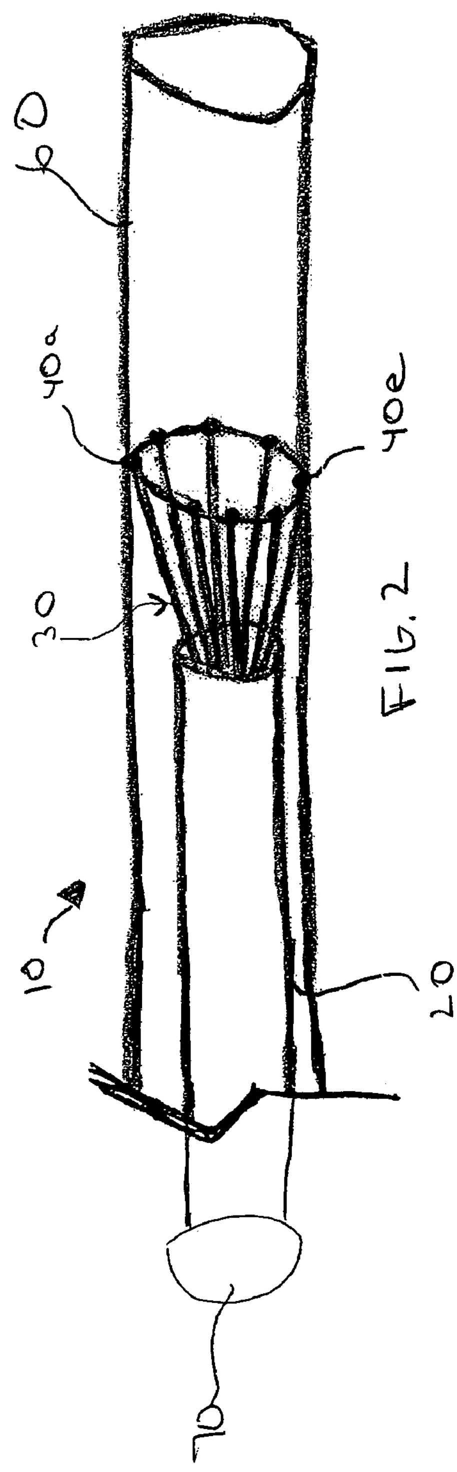
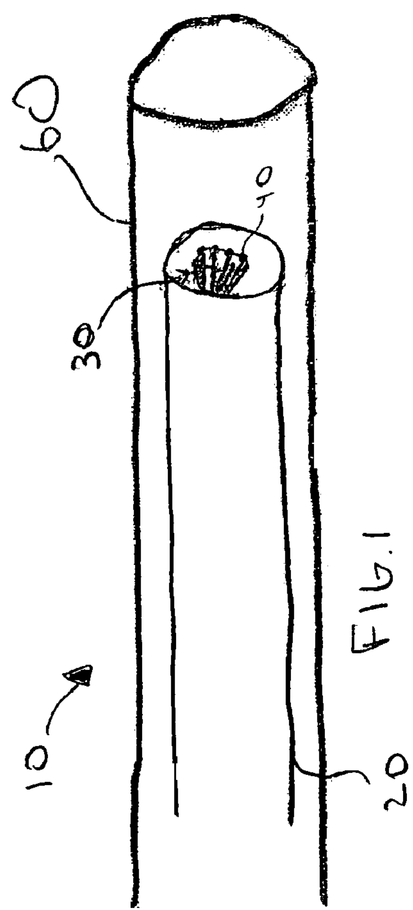

40 b
40 a
50
40 c
40h
40d
40g
40e
40f

INTRALUMINAL ELECTRODE ASSEMBLY

CROSS-REFERENCE TO RELATED APPLICATIONS

The present application claims priority to U.S. Provisional Application No. 60/608,513, filed on Sep. 10, 2004, which is incorporated by reference herein.

FIELD OF THE INVENTION

The present invention is directed to an expandable intraluminal electrode assembly.

BACKGROUND OF THE INVENTION

Neuromodulation, which involves delivering electrical impulses to neural target sites, has become an important therapeutic method and is an option when other forms of treatment, such as drug administration, are ineffective. Neuromodulation has revolutionized the treatment of several neurological disorders, such as movement disorders and chronic pain and has been described in U.S. Pat. No. 6885,888 for treating heart contractility. Technical and mechanical limitations, however, create obstacles to the final application of such methods in patients. For example, one obstacle is in the invasive nature of neuromodulation, which requires open surgery.

As such, there is a need for further approaches for neuromodulation, particularly minimally invasive approaches.

SUMMARY OF THE INVENTION

In an embodiment, the present invention provides an intraluminal electrode assembly comprising a cannulated tube and a plurality of wires disposed in the cannulated tube. Each of the plurality of wires has one of a plurality of electrical contacts at a distal end thereof. The plurality of wires assumes a radially constrained configuration within the cannulated tube in a retracted position and a radially extended configuration outward of the cannulated tube in a deployed position. The electrode assembly further comprises a spring wire connecting the plurality of electrical contacts together to collectively form a substantially circular configuration in a deployed position.

BRIEF DESCRIPTION OF THE DRAWINGS

The present invention will become more fully understood from the detailed description given hereinbelow and the accompanying drawings which are given by way of illustration only. It should be understood that the present invention is in no way limited to the particular arrangement or inclusion of components depicted in the accompanying drawings and wherein:

FIG. 1 depicts a perspective view of an embodiment of an intraluminal electrode assembly according to the present invention in a retracted position.

FIG. 2 depicts a perspective view of an embodiment of an intraluminal electrode assembly according to the present invention in a deployed position.

DETAILED DESCRIPTION OF THE INVENTION

Figure 3:
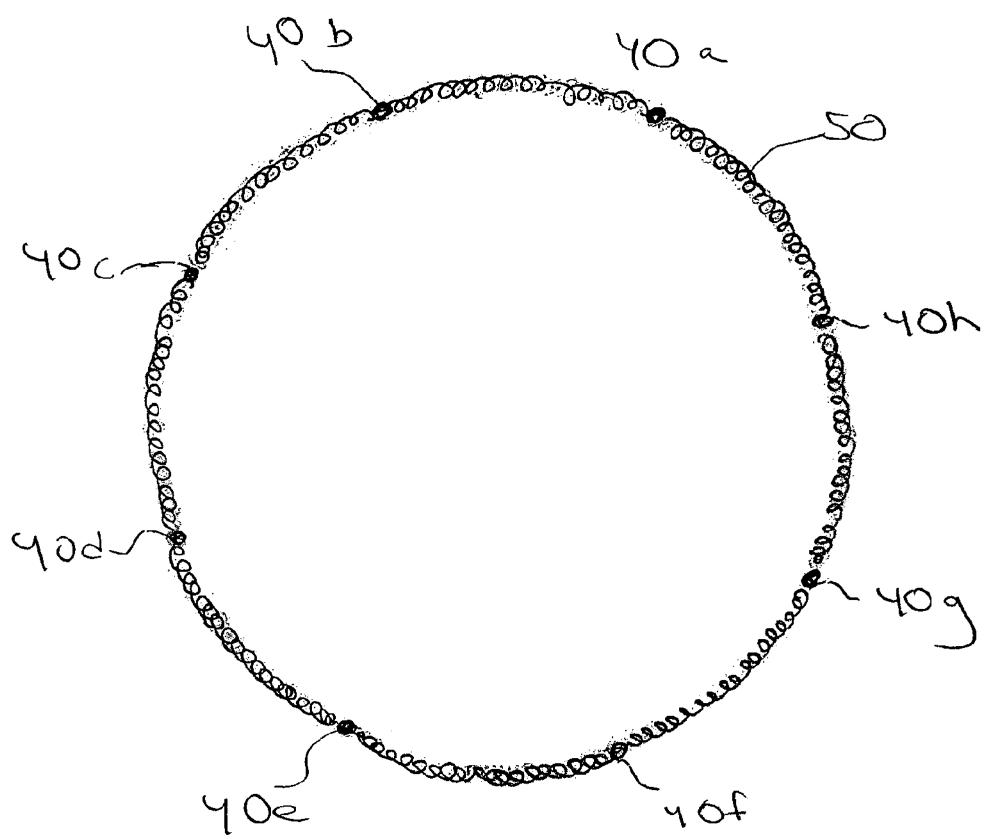
FIG. 3 depicts an end view of an embodiment of an intraluminal electrode assembly according to the present invention.

Referring to FIGS. 1-3, the present invention provides an electrode assembly 10 comprising a cannulated tube 20, which can be a catheter, housing a plurality of wires 30. Each of the plurality of wires 30 has one of a plurality of electrical contacts 40 at a distal end thereof. Referring specifically to FIG. 1, in a retracted position, the plurality of wires 30 assumes a radially constrained configuration within cannulated tube 20. Referring to FIG. 2, in a deployed position, the distal portion of plurality of wires 30 assumes a radially extended configuration outward of cannulated tube 20. As seen from the end view of electrode assembly 10 in FIG. 3, a spring wire 50 connects the plurality of electrical contacts 40 (depicted as electrical contacts 40*a*-40*g*) together to form a substantially circular configuration in a deployed position. In an embodiment, plurality of wires 30, or at least the distal portion of plurality of wires 30 having electrical contacts 40 are fabricated from a shape memory material to allow the distal portion to project concentrically out of cannulated tube 20. Of course, other mechanisms for allowing the distal portion of plurality of wires 30 having electrical contacts 40 to project radially outward from cannulated tube 20 can be employed.

Although electrode assembly 10 is not necessarily limited to any particular use, the substantially circular configuration of the distal end of deployed plurality of wires 30 allows electrode assembly 10 to be used for intraluminal purposes, such as transvascular electrical neuromodulation of a target site adjacent to a vessel. Specifically, referring to FIG. 1, electrode assembly 10 can be inserted into a vessel 60 and urged distally forward. Referring to FIG. 2, upon reaching the desired point in vessel 60, plurality of wires 30 can be deployed to project radially outward to reach and contact the walls of vessel 60. Since all the plurality of wires 30 have the same shape, the final resulting vector drives the distal portion of plurality of wires 30 out from cannulated tube 20 to contact the wall of vessel 60.

In a preferred embodiment, plurality of wires 30 comprises six to eight wires. Further preferably, each of the plurality of electrical contacts 40 of the plurality of wires 30 can be selectively activated such that select electrical contacts 40 on one segment of the arc of the distal end of the plurality of wires 30 can be activated to apply focused electrical signals on a desired side of a vessel. The selective powerability over each electrical contact 40 may be achieved by employing a system including a programmer coupled via a conductor to a telemetry antenna. The programmer is capable of sending signals via the telemetry antenna to control the electrical signal delivered to electrical contacts 40. Such a system permits the selection of various pulse output options after electrode assembly 10 is positioned using telemetry communications. The present invention also contemplated radiofrequency systems to selectively power electrical contacts 40.

As will be understood by one of skill in the art, the independent powerability of electrical contacts 40 also provides a practitioner with means of modifying or steering the direction and locus of application of electrical signals to precisely target portions of the target region to achieve desired therapy. For example, with reference to FIG. 2, electrical contact 40*a* may be powered to apply an electrical signal to an area adjacent thereto while the signal to electrical contact 40*e* may be substantially minimized to reduce or stop the application of an electrical signal to an area adjacent to electrical contact 40*e*. Because the locus of stimulation can be selectively adjusted and/or steered in this embodiment of electrode assembly 10, specific areas of the target region can be precisely targeted to achieve the desired therapy. Other or additional means of selectively steering the application of electrical signals may also be utilized in the present invention, such as the methods described in U.S. Pat. No. 5,713,922, which is incorporated by reference herein.

Referring to FIG. 2, in a preferred embodiment, the proximal end of each of the plurality of wires 30 is in communication with rotator 70 at the proximal end of cannulated tube 20 such the distal end of the plurality of wires 30 can be rotated by similar motion of rotator 70. For example, rotator 70 could be a rotary motor or a manual dial that transfers rotational motion from rotator 70 to the distal end of the plurality of wires 30.

The present invention also provides an electrode assembly system including electrode assembly 10 and further including components useful in identifying, monitoring, or affecting a target region. For example, such a system could include a component for lesioning and temperature monitoring, and/or a component that has a fiberoptic monitor which allows telemetric intracranial monitoring capabilities, and/or a microelectrode recording component, and/or a sensing component to incorporate a feedback mechanism to assist in determining whether electrical contacts 40 should be adjusted. With respect to a sensing component, a sensor can be incorporated with the electrode assembly system according to the present invention. The sensors can be used with a closed-loop feedback system in order to automatically determine the level of electrical signal to apply to provide the desired therapy. The sensors may be implanted or positioned in or at a portion of the patient's body suitable for detecting characteristics, symptoms or attributes of the condition or disorder being treated, for example, such as electrical brain activity, cerebral blood flow, and/or vital signs or other chemical and electrical activity of the body. Sensors suitable for use in a system according to the present invention include, for example, those disclosed in U.S. Pat. No. 5,711,316, which is incorporated by reference herein. In cases where the attribute of the symptom is the electrical activity of the brain, stimulating electrodes may be intermittently used to record electrical activity. Alternatively, one or more electrodes implanted or positioned within the brain may serve as a sensor or a recording electrode. When necessary, these sensing or recording electrodes may deliver stimulation therapy to the target region. The output of an external feedback sensor may communicate with a pulse generator through a telemetry down-link. Any sensing functions in accordance with the present invention can be performed locally, distally, or remotely from the target site. The present invention also contemplates use of electrode assembly 10 integrated with imaging methods known in the art such as X-rays, computer tomography, magnetic resonance imaging, and functional magnetic resonance imaging.

Electrode assembly 10 may also be implemented within a drug delivery system to provide chemical stimulation utilizing a drug, pharmaceutical, or therapeutic agent. In this embodiment, the signal generator is replaced with or includes a pump and electrical contacts 10 are replaced with a drug ports. The pump may be implanted below the skin of a patient and may have a port into which a hypodermic needle can be inserted through the skin to inject a quantity of a liquid, such as a drug, pharmaceutical, or therapeutic agent. The liquid agent is delivered from a pump through a catheter port into a catheter. Alternatively, the pump may be located outside of the patient's body. The catheter is positioned to deliver the liquid agent to specific infusion sites in the brain or other target site. Alternatively, electrode assembly 10 may be combined with a drug delivery system to provide both chemical and electrical signals to target regions.

Figure 4:
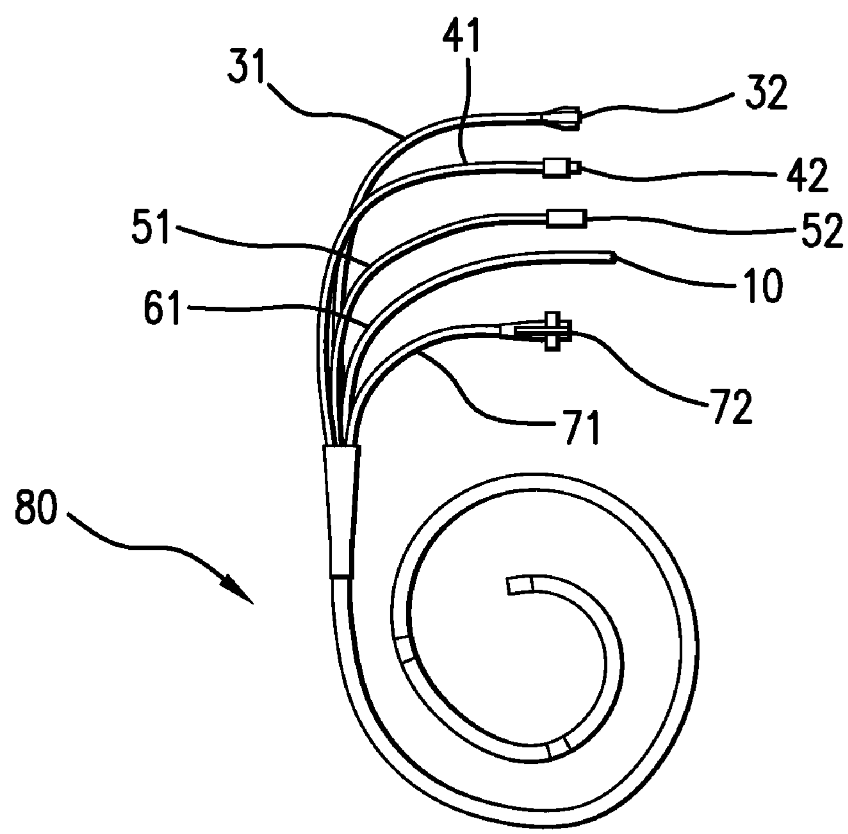
FIG. 4 depicts a pulmonary artery catheter including an embodiment of an intraluminal electrode assembly according to the present invention.

Referring to FIG. 4, in another embodiment, the present invention provides a catheter 80 having multiple lumens, wherein one of the multiple lumens houses electrode assembly 10. In a preferred embodiment, catheter 80 is a pulmonary artery catheter, such as a Swan-Ganz type pulmonary artery catheter, wherein the multiple lumens allow for the measurement of cardiac output, pulmonary pressure, atrial pressure, and for providing an electrical signal to a target site adjacent a lumen. Specifically, in an embodiment catheter 80 comprises a thermistor lumen 31 housing a thermistor 32 to measure cardiac output; a pulmonary artery distal lumen 41 housing a sensor 42 to measure pulmonary artery pressure or pulmonary capillary wedge pressure; a proximal right atrial lumen 51 housing a sensor 52 to measure right atrial or central venous pressure; a balloon lumen 71 housing a balloon 72 to isolating the right chamber of the heart from the left chamber; and an electrode lumen 61 housing electrode assembly 10.

Figure 5:
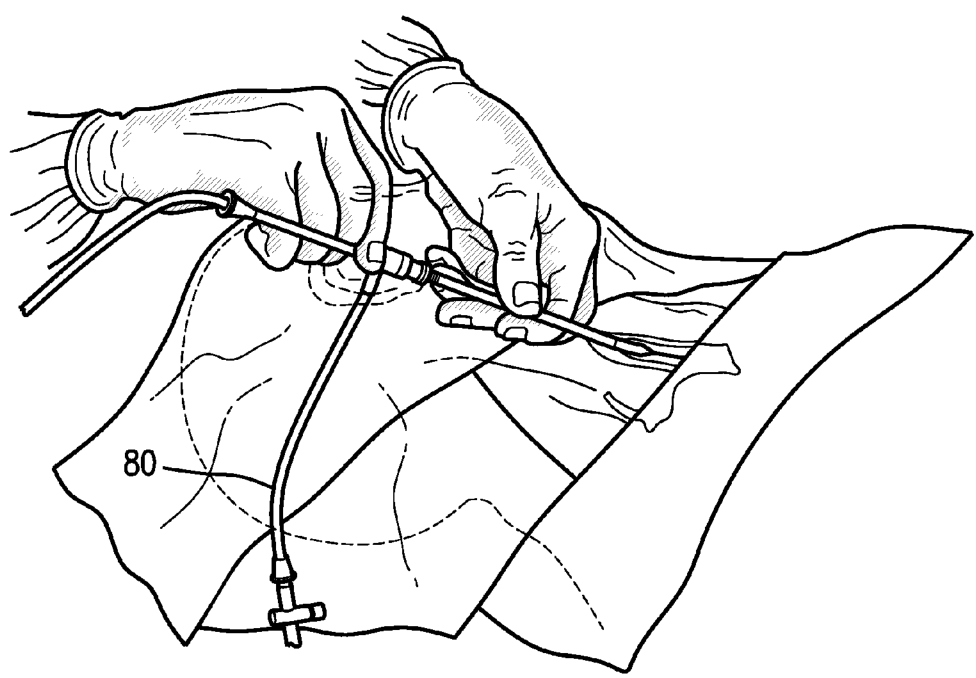
FIG. 5 illustrates a step from an exemplary method of delivering a pulmonary artery catheter including an embodiment of an intraluminal electrode assembly according to the present invention.
Figure 6:
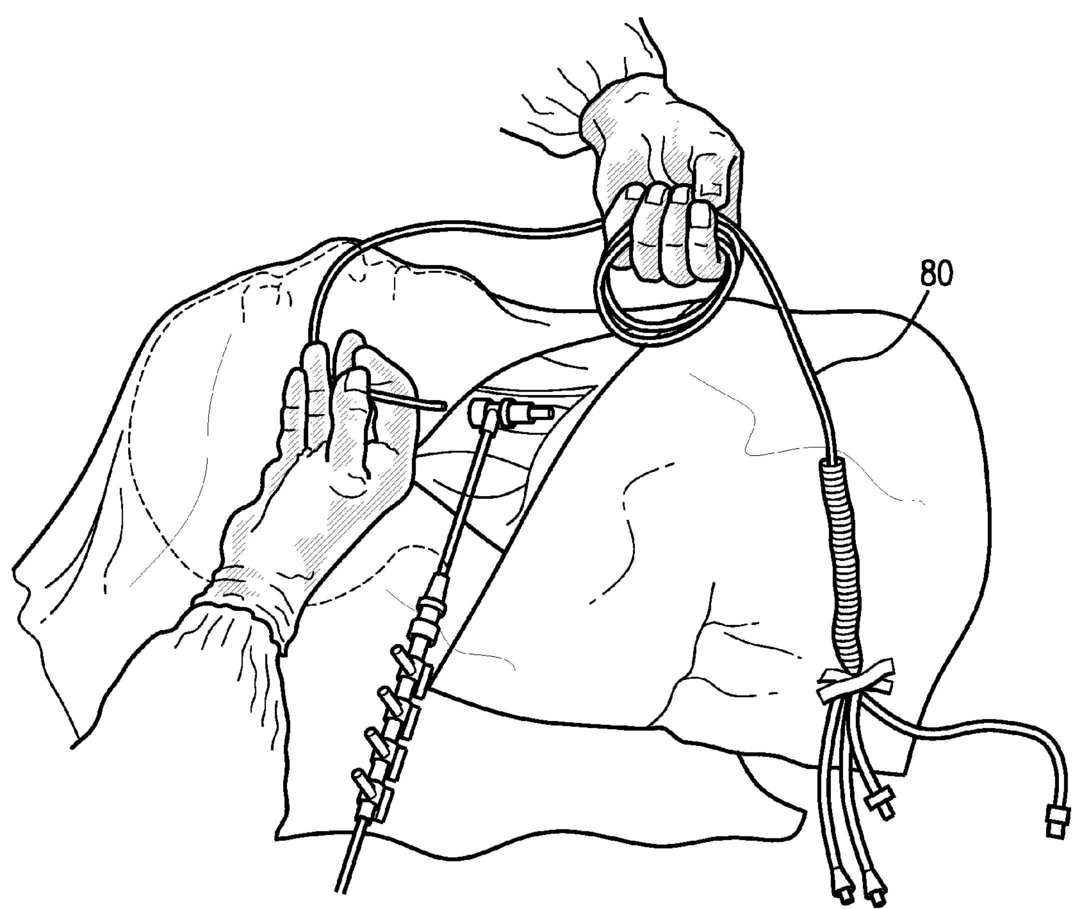
FIG. 6 illustrates a step after the step illustrated in FIG. 5 from an exemplary method of delivering a pulmonary artery catheter including an embodiment of an intraluminal electrode assembly according to the present invention.

In an exemplary method of using catheter 80 in a pulmonary artery, catheter 80 is delivered and implanted in a manner similar to the delivery and implantation process used in currently available pulmonary artery catheters. Referring to FIG. 5 and FIG. 6, after venous access, catheter 80 is passed through an introducer up to a 20 cm mark. Then, balloon 72 at the distal end of balloon lumen 71 is inflated and pressure and tracings are recorded. As soon as catheter 80 is advanced to the point where the inflated balloon 72 occludes the pulmonary artery, a wedge pulmonary pressure can be obtained from the sensor of pulmonary artery distal lumen 41. This pressure indication provides the physician the necessary feedback that the distal end of catheter 80 is well positioned in the pulmonary artery. Once adequate positioning is achieved, the electrode assembly 10 is urged forward out from electrode lumen 61 to the walls of the pulmonary artery. X-ray and fluoroscopy can be used to aid in positioning catheter 80. Such a method could be used to apply an electrical signal to a target site adjacent a pulmonary nerve, such as cardiac nerves to modulate the activity thereof. Of course, such a method of delivering catheter 80 is only exemplary and catheter 80 is not limited by any particular method of delivery and implantation.

The foregoing description has been set forth merely to illustrate the invention and are not intended as being limiting. Each of the disclosed aspects and embodiments of the present invention may be considered individually or in combination with other aspects, embodiments, and variations of the invention. In addition, unless otherwise specified, none of the steps of the methods of the present invention are confined to any particular order of performance. Further, although electrode assembly 10 is occasionally described with respect to neuromodulation, electrode assembly 10 is not limited to this particular use. Modifications of the disclosed embodiments incorporating the spirit and substance of the invention may occur to persons skilled in the art and such modifications are within the scope of the present invention. For example, although catheter 80 is described as have a balloon lumen 71 with a balloon 72 at the distal end thereof, other embodiments can include catheter 80 having multiple lumens without a balloon. Furthermore, all references cited herein are incorporated by reference in their entirety.

We claim:

1. An electrode assembly comprising:

a cannulated tube;

a plurality of wires disposed within the cannulated tube, each of the plurality of wires having one of a plurality of electrical contacts disposed on a distal end thereof, the distal portion of the plurality of wires assuming a radially constrained configuration within the cannulated tube in a retracted position and a radially extended position outward of the cannulated tube in a deployed position; and a spring electrode having a substantially circular shape and connecting the plurality of electrical contacts to collectively form a substantially circular configuration in a deployed position.

2. The electrode assembly of claim 1, wherein the plurality of wires comprises six to eight wires.

3. The electrode assembly of claim 1, wherein the plurality of wires is fabricated from a shape memory material.

4. The electrode assembly of claim 1, wherein a proximal end of the plurality of wires is connected to a rotator at a proximal end of the cannulated tube to transfer rotational motion from the rotator to the plurality of wires.

5. The electrode assembly of claim 1, wherein each of the electrical contacts is selectively powerable.

6. A catheter comprising multiple lumens, one of the multiple lumens housing the electrode assembly of claim 1.

7. The catheter of claim 6, wherein the multiple lumens comprise:

a thermistor lumen housing a thermistor to measure cardiac output;

a pulmonary artery distal lumen housing a sensor to measure pulmonary artery pressure or pulmonary capillary wedge pressure;

a proximal right atrial lumen for housing a sensor to measure right atrial or central venous pressure;

a balloon lumen housing a balloon to isolating the right chamber of the heart from the left chamber; and an electrode lumen housing the electrode assembly.

* * * * *